(12) United States Patent
Mantell

(10) Patent No.: US 7,704,223 B2
(45) Date of Patent: Apr. 27, 2010

(54) SYSTEM AND METHOD FOR DELIVERING A SUBSTANCE TO A BODY CAVITY

(75) Inventor: Robert R. Mantell, Arlington Heights, IL (US)

(73) Assignee: Northgate Technologies Inc., Elgin, IL (US)

( * ) Notice: Subject to any disclaimer, the term of this patent is extended or adjusted under 35 U.S.C. 154(b) by 1117 days.

(21) Appl. No.: 10/961,475

(22) Filed: Oct. 7, 2004

(65) Prior Publication Data

US 2005/0137529 A1 Jun. 23, 2005

Related U.S. Application Data

(60) Provisional application No. 60/509,733, filed on Oct. 7, 2003.

(51) Int. Cl.
*A61M 37/00* (2006.01)
(52) U.S. Cl. .......................................... 604/24; 604/26
(58) Field of Classification Search .................. 604/23, 604/24, 26, 93.01
See application file for complete search history.

(56) References Cited

U.S. PATENT DOCUMENTS

| 2,722,935 | A | 11/1955 | Thompson et al. |
|---|---|---|---|
| 3,464,434 | A | 9/1969 | Nielsen |
| 3,853,105 | A | 12/1974 | Kenagy |
| 3,862,907 | A | 1/1975 | Shimotsuma et al. |
| 3,982,533 | A | 9/1976 | Wiest |
| 4,048,992 | A | 9/1977 | Lindemann et al. |
| 4,109,656 | A | 8/1978 | Goethel et al. |
| 4,207,887 | A | 6/1980 | Hiltebrandt et al. |
| 4,245,979 | A | 1/1981 | Ito |
| 4,464,169 | A | 8/1984 | Semm |

(Continued)

FOREIGN PATENT DOCUMENTS

EP 0 369 764 B1 6/1994

(Continued)

OTHER PUBLICATIONS

U.S. Appl. No. 10/696,675, filed Oct. 28, 2003, entitled "Dual-Capacity Insufflator Tube".

(Continued)

*Primary Examiner*—Nicholas D Lucchesi
*Assistant Examiner*—Christopher D Koharski
(74) *Attorney, Agent, or Firm*—Brinks Hofer Gilson & Lione

(57) ABSTRACT

A system and method for creating a medicated atmosphere in an organ, or body cavity is disclosed. The system includes a flexible aerosolization catheter, a device for introducing of the aerosolization catheter, a medication delivery apparatus configured to control delivery of a medication to the catheter, a gas delivery apparatus in communication with the catheter, a gas pressure relief apparatus configured to relieve pressure in the organ or body cavity, and a central controller in communication with the medication delivery apparatus, gas delivery apparatus, and gas pressure relief apparatus. The method includes providing insufflation gas and an aerosol of medication to an organ or body cavity while controlling overall pressure in the organ or cavity. The method may also include re-entering a patient through at least one port to apply gas and an aerosolized medicament, in either a post-operative procedure or in a chemotherapy context.

14 Claims, 10 Drawing Sheets

U.S. PATENT DOCUMENTS

| | | | |
|---|---|---|---|
| 4,640,260 A | 2/1987 | Perez | |
| 4,676,774 A | 6/1987 | Semm et al. | |
| 4,691,900 A | 9/1987 | Maeda | |
| 4,699,173 A | 10/1987 | Röhling | |
| 4,878,894 A | 11/1989 | Sutter, Jr. et al. | |
| 4,884,565 A | 12/1989 | Cocozza | |
| 4,905,497 A | 3/1990 | Shindo et al. | |
| 4,960,134 A | 10/1990 | Webster | |
| 4,977,776 A | 12/1990 | Shindo et al. | |
| 5,006,109 A | 4/1991 | Douglas et al. | |
| 5,031,613 A | 7/1991 | Smith et al. | |
| 5,061,239 A | 10/1991 | Shiels | |
| 5,121,700 A | 6/1992 | Blackwell et al. | |
| 5,152,745 A | 10/1992 | Steiner et al. | |
| 5,246,419 A * | 9/1993 | Absten | 604/26 |
| 5,250,287 A | 10/1993 | Cocozza | |
| 5,273,531 A | 12/1993 | Knoepfler | |
| 5,292,304 A | 3/1994 | Mantell et al. | |
| 5,305,698 A | 4/1994 | Blackwell et al. | |
| 5,328,458 A | 7/1994 | Sekino et al. | |
| 5,342,299 A | 8/1994 | Snoke et al. | |
| 5,360,396 A | 11/1994 | Chan | |
| 5,362,310 A | 11/1994 | Semm | |
| 5,363,839 A | 11/1994 | Lankford | |
| 5,383,923 A | 1/1995 | Webster | |
| 5,411,474 A | 5/1995 | Ott et al. | |
| 5,411,988 A | 5/1995 | Bockow et al. | |
| 5,439,441 A | 8/1995 | Grimsley et al. | |
| 5,464,008 A | 11/1995 | Kim | |
| 5,478,837 A | 12/1995 | Rodgers et al. | |
| 5,496,408 A | 3/1996 | Motoda et al. | |
| 5,514,087 A | 5/1996 | Jones | |
| 5,534,261 A | 7/1996 | Rodgers et al. | |
| 5,537,993 A | 7/1996 | Reichert et al. | |
| 5,542,412 A | 8/1996 | Century | |
| 5,554,112 A | 9/1996 | Walbrink et al. | |
| 5,558,668 A | 9/1996 | Lankford et al. | |
| 5,578,305 A | 11/1996 | Franz et al. | |
| 5,586,974 A | 12/1996 | Martinez et al. | |
| 5,599,297 A | 2/1997 | Chin et al. | |
| 5,642,730 A | 7/1997 | Baran | |
| 5,664,560 A | 9/1997 | Merrick et al. | |
| 5,728,223 A | 3/1998 | Murakami et al. | |
| 5,800,381 A | 9/1998 | Ognier | |
| 5,873,819 A | 2/1999 | Koch | |
| 5,934,274 A | 8/1999 | Merrick et al. | |
| 5,964,223 A | 10/1999 | Baran | |
| 5,979,474 A | 11/1999 | Manako | |
| 5,980,835 A | 11/1999 | Porozni | |
| 6,051,241 A | 4/2000 | Briend et al. | |
| 6,068,703 A | 5/2000 | Chen et al. | |
| 6,076,745 A | 6/2000 | Primdahl | |
| 6,079,413 A | 6/2000 | Baran | |
| 6,085,556 A | 7/2000 | Moon | |
| 6,092,364 A | 7/2000 | Stellwagen | |
| 6,116,240 A | 9/2000 | Merrick et al. | |
| 6,165,201 A * | 12/2000 | Sawhney et al. | 606/214 |
| 6,203,519 B1 | 3/2001 | Fagerström et al. | |
| 6,240,943 B1 | 6/2001 | Smith | |
| 6,267,746 B1 | 7/2001 | Bumbalough | |
| 6,299,592 B1 | 10/2001 | Zander | |
| 6,379,373 B1 | 4/2002 | Sawhney et al. | |
| 6,428,500 B1 | 8/2002 | Koninckx | |
| 6,526,976 B1 | 3/2003 | Baran | |
| 6,537,246 B1 | 3/2003 | Unger et al. | |
| 6,579,279 B1 | 6/2003 | Rabiner et al. | |
| 6,679,873 B2 | 1/2004 | Rabiner et al. | |
| 6,719,960 B1 | 4/2004 | Hills et al. | |
| 6,729,334 B1 | 5/2004 | Baran | |
| 6,802,835 B2 | 10/2004 | Rabiner et al. | |
| 7,027,851 B2 | 4/2006 | Mejia | |
| 2002/0082584 A1 | 6/2002 | Rosenman et al. | |
| 2002/0183715 A1 | 12/2002 | Mantell et al. | |
| 2005/0010164 A1 | 1/2005 | Mantell | |
| 2005/0125002 A1 | 6/2005 | Baran et al. | |

FOREIGN PATENT DOCUMENTS

| | | |
|---|---|---|
| EP | 692 273 B1 | 1/1996 |
| EP | 0 937 478 A1 | 8/1999 |
| EP | 0 712 635 B1 | 5/2003 |
| EP | 1 477 119 A1 | 11/2004 |
| FR | 2 840 222 | 12/2003 |
| JP | 5-168714 | 2/1993 |
| JP | 63-84243 | 6/1998 |
| WO | WO 93/17744 | 9/1993 |
| WO | WO 94/00484 | 1/1994 |
| WO | WO 96/29987 | 10/1996 |
| WO | WO 96/40090 | 12/1996 |
| WO | WO 00/69511 | 11/2000 |

OTHER PUBLICATIONS

International Search Report for Application No. PCT/US2004/033024 dated Feb. 17, 2005.

Claims for U.S.Appl. No. 10/978,692, filed Nov. 1, 2004 entitled "System And Method For Manipulating A Catheter For Delivering A Substance To A Body Cavity".

European Search Report Dated Jun. 12, 2008—EP 04798753.2.

* cited by examiner

SYSTEM AND METHOD FOR DELIVERING A SUBSTANCE TO A BODY CAVITY

CROSS-REFERENCE TO RELATED APPLICATION

This application claims the benefit of U.S. Provisional Application 60/509,733, filed Oct. 7, 2003, the entirety of which is incorporated herein by reference.

FIELD OF THE INVENTION

The present invention relates to a system and method for delivering a substance to a body cavity. More particularly, the present invention relates to a system and method for delivering a substance to a body cavity in conjunction with a minimally invasive operative procedure or for therapeutic treatment unrelated to a surgical procedure.

BACKGROUND

Among problems that physicians have encountered during diagnostic or surgical procedures, using both "open" techniques, and minimally invasive (laparoscopic) surgical techniques, are numerous post procedural complications. These complications can consist of, but are not limited to, post operative pain, infections, tissue adhesions, and tumor formation. Numerous products, such as medications and associated delivery systems, addressing these issues exist on the market to improve the surgical or invasive experience and patient outcomes. Among these products are suction and irrigation wands that are used for flushing tissue sites with sterile water or saline and removing blood. There are medications, which are spread over exposed organs, to coat or provide a barrier between tissue and organs for prevention of adhesions. These materials may be in gel form, sheet form, spray (liquid) form, or aerosol form to coat organs or tissues, or to provide thin layer deposition to the organs in the operative site. Some of these materials may be used in both open and minimally invasive surgical techniques.

The problems with these materials, and their application as related to laparoscopy, are their inability to be used easily and effectively in a minimally invasive laparoscopic environment. Among the difficulties associated with spraying of liquids, is the pooling and lack of containment of the fluids used with irrigation and aspiration wands. It is also difficult to cover large areas (greater than several square centimeters), and do so without using much more medicament than is necessary. This contributes to the cost of excessive medication, and adding to the cost and time of the surgery.

Materials used in sheet form are not practical to apply to the organs when using laparoscopic minimally invasive techniques, due to the difficulty in getting the material through standard trocars, and then spreading the material out over the affected area, and keeping it in place once positioned. The liquid spray technique has many of the same problems as the irrigation approach. These devices normally force a liquid through a cannula like device under pressure. The introduction of additional fluid into the body cavity can cause increases in pressure and do not include a means for pressure relief. Without a means for directing the spray, it is difficult to control where the medication is deposited, and in what amount. Also, the precise disposition of the medication as to amount and location is difficult to control.

Compound materials are sometimes mixed prior to being aerosolized by a hand held syringe device, and then by applying an air stream to the mixed medication as it is being dispensed, to create an aerosolized stream that is used to "paint" the organs. This method also ignores the problem of the creation of additional pressure in the organ with no relief mechanism. Creating an aerosol "cloud" contends with the problem of how to effectively coat all the surfaces required, but also introduces the problem of increasing abdominal pressures uncontrollably inside an insufflated body cavity or organ, such as the peritoneum.

All of the above methodologies, while focused on applying substances in different physical forms for the purpose of treating or coating tissues and/or organs, have not been optimized for use in the laparoscopic, minimally invasive environment. The term "substance", as used in this specification, includes, without limitation, a liquid, powder or gas, or any combination thereof.

BRIEF SUMMARY

In order to address the deficiencies in the prior art, a system and method for providing a substance to a body cavity is discussed below. According to a first aspect of the invention, a system is provided that will allow the application of a substance, such as an aerosolized medicament to a distended body cavity that will allow for the efficient, safe, and effective application of any number of substances, such as aerosolized liquids, which can be used for pain management (analgesics), infection prevention (prophylactic antibiotics), tissue adhesion (any number of formulations can be used including naturally occurring lubricious medications such as hyaluronic acid, or any number of other medicaments such as heparin, glycerin or glycol medications, or even humidity), and tumor prevention (using targeted or prophylactic chemotherapy drugs or methods). A pressure relief or maintenance device controllably keeps the pressure within a desired range, compensating for the introduction of substances into the body cavity that can build up unwanted pressure. A central controller in communication with a substance introducing device and an insufflator may coordinate all of the parameters of pressure, flow, temperature and so on.

According to another aspect of this invention, a method for providing continued or postoperative application of a substance, by re-instituting an environment in the patient in which subsequent applications of medication may be administered, is disclosed. The method includes providing a patient with a port or other device that will fasten to the outer abdomen wall and the interior abdomen wall to provide a passage into a body cavity of a patient. A supply of insufflation gas is provided through the port and a substance is introduced, for example in aerosol form, into the body cavity through the port. In one embodiment the substance is introduced via a nebulizing catheter. In one embodiment, the method may relate to a therapeutic treatment for cancerous tumors and the substance supplied to the body cavity may be chemotherapy medication. In another embodiment, the method may be related to post-operative pain or infection treatment, such as the application of analgesic or antibiotic substances, respectively.

In yet a further aspect of this invention a method and system are disclosed that improve upon typical methods of applying medications to an insufflated organ by controlling and coordinating the requirements of pressure maintenance and relief within the organ, coordinating the application of the aerosolized medicament within the patient (including the amount, rate of application, timing of the administration of the medicament, and control of the direction or formation of an optimized aerosolized laparoscopic medicated environment), maintaining proper distention for visualization and operative manipulation of instruments, and providing feedback (visual and or audible) on the information or data required for controlling the operative, diagnostic, or post operative treatment of a patient.

Further aspects and advantages of the invention are discussed below in conjunction with the preferred embodiments.

DETAILED DESCRIPTION OF THE PRESENTLY PREFERRED EMBODIMENTS

Figure 1:
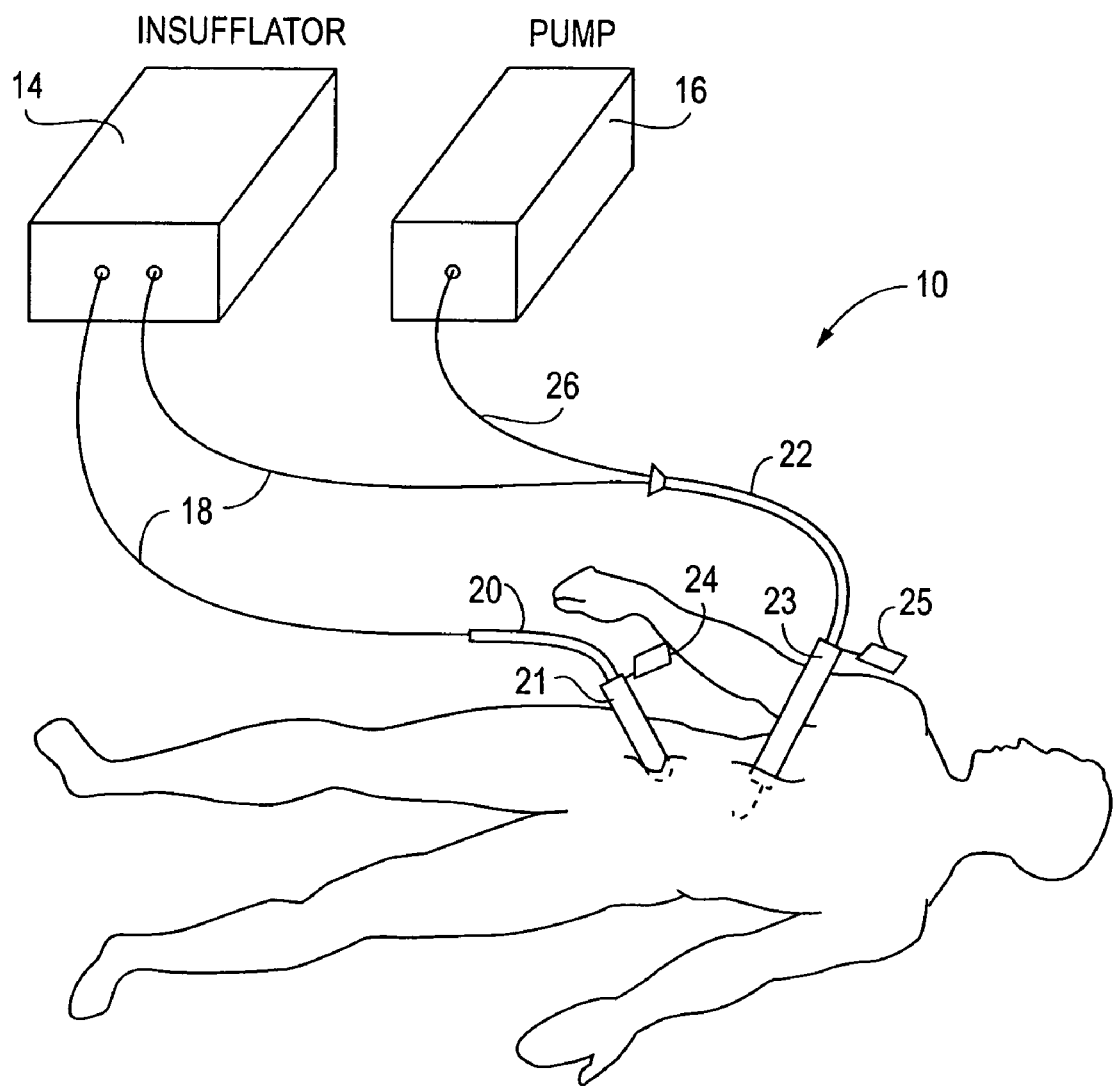
FIG. 1 illustrates an embodiment of fluid connections in a system for laparoscopic delivery of aerosolized medication according to one embodiment of the present invention.

Referring to FIG. 1, an embodiment of a system 10 for delivery of a substance to a body cavity is shown connected to a patient 12. The system 10 includes an insufflator 14 for providing a supply of insufflation gas to the patient 12. The system also includes a pump 16 configured to controllably supply a medicament to the patient 12. The insufflator 14 connects to gas delivery lines 18 and then to one or more catheters 20, 22. The insufflator 14 may include an integrated gas temperature control mechanism or may be combined with one or more in-line gas heaters to control the temperature of gas supplied for insufflation and/or nebulization. A first catheter is an insufflation catheter 20 sized for cooperating with a trocar 21 or other standard catheter insertion needle so that the insufflation catheter may be directed into the peritoneum or other specific location in the patient 12. A pressure relief control valve 24 is positioned along the supply of insufflation gas, for example on the catheter 20 or trocar 21, so that pressure in the peritoneum or other target location in the patient will be monitored and adjusted to maintain a desired level.

An aerosolization gas supply, preferably separately controllable from the general insufflation gas sent through the gas delivery line 18 to the nebulization catheter 22, is also supplied by the insufflator 14. This aerosolization gas supply is directed through a gas line 18 connected to a nebulization catheter 22 inserted into the peritoneum through another trocar 23 or other suitable needle. Although the system 10 may operate with a single pressure relief control valve positioned anywhere along the components making up the insufflation gas supply chain, a separate and independently controllable pressure relief valve 25 may be positioned on the nebulization gas supply, such as at the trocar 23 for the nebulization catheter 22. The nebulization catheter receives a medicament in fluid form from fluid supply line 26 connected with the pump 16. The gas provided to the nebulizing catheter is mixed with a fluid medicament supplied by the pump 16 and generates a nebulized medicament for deposit on specific organs, on the peritoneum cavity wall and other locations within the patient 12. The system of FIG. 1 is shown with only the basic fluid and gas lines for clarity. A central controller, described in greater detail below, coordinates the actions of the insufflator, pump, and pressure relief control valve(s) so that any of the system parameters, such as pressure, gas or fluid flow rate, temperature and so on, may be managed. Although a nebulizing catheter is shown, any of a number of other devices for introducing a substance into a body cavity may also be used. For example, the nebulizing catheter 22 may be replaced by a suction irrigation wand to infuse the body cavity with a substance.

The insufflator 14 may be any of a number of insufflators, such as the OMNIFLATOR Model 6620 available from Northgate Technologies, Inc. of Elgin, Ill. Examples of suitable insufflators are described in U.S. Pat. No. 6,299,592 and U.S. application Ser. No. 10/829,485, and the entirety of each of these references are incorporated by reference. The insufflator may include a pressurized source of insufflation gas. Examples of insufflation gases include, but are not limited to, carbon dioxide, nitrous oxide, argon, or helium. The insufflation gas is typically reduced in pressure by the insufflator to approximately 45 to 55 millimeters of mercury (also know as a "push" pressure), although the pressure may be changed depending on the insufflator in use and any regulations that may be in force. While the push pressure may be in the range of 45-55 millimeters of mercury, the actual pressure maintained in the peritoneum or other body cavity is preferably less than 25-30 mm of mercury and, in the case of many laparoscopic surgeries, most preferably in the range of 12 mm of mercury.

The pump 16 may be a peristaltic pump, syringe pump, hydraulic (air over liquid) pump or any other mechanism capable of controlling the dispensing of medication. Controllable pump parameters may include the rate and volume, as well as the timing, of delivery. It is contemplated that continuous and periodic pumping may be desired. Delayed pumping of medication, such as the transport of medication to the nebulization catheter 22 at predetermined times for predetermined intervals is also contemplated. In one embodiment, the pump may include a heating mechanism to heat the fluid to a controlled temperature prior to delivery to the fluid line 26 and nebulizing catheter 22.

The gas and fluid lines 18, 26 may be constructed from disposable polyvinyl chloride tubes, although in other embodiments any suitable materials may be used. For example, the tubing may be made of a silicone material that is reusable. The diameters of the tubes may be varied depending on flow rate requirements and any regulations that are in force. Also, the inner diameter of each of the tubes may be different from each other. A filter (not shown) may be located in each of the tubes used for the gas lines 18 to provide a particulate barrier. In one embodiment, the filter may be a glass-fiber hydrophobic filter that provides a particulate barrier of approximately 0.2 microns and operates at a ninety-nine percent rate of efficiency. In other embodiments any number of commonly used filters, with different filtering capabilities, may also be used.

The pressure relief valves (PRV's) 24, 25 associated with the insufflation and aerosolization gas supplies, respectively, may be located within the gas supply lines 18 or the catheters 20, 22. In other embodiments the valves 24, 25 may each be a discrete valve such as commonly available from Pneutronics, a division of Parker Hannifin Corporation of Cleveland, Ohio. Any of a number of types of valves may be used. For example, the valve may be operated electrically, pneumatically, or hydraulically. In other embodiments, the valve may be a mechanical pressure relief valve preset to relieve pressure once a preset maximum has been reached. For example, when the pressure of the insufflation gas reaches a preset pressure, a spring operated valve opens and provides pressure relief. Preferably, the valve is operated by a signal generated by a controller associated with the electronics of the insufflator. An example of such a controller is contained within the control circuitry of the Northgate OMNIFLATOR 6620 Insufflator, and an example of such a valve is a pinch valve. The signal is generated via feedback due to the monitoring of flow restriction or back pressure sensed by a central controller 130 (See FIG. 5). The monitoring of the pressure of the insufflation gas is accomplished via a pressure transducer (not shown) in the controller 130 that monitors the pressure.

The nebulizing catheter 22 preferably includes a combination of at least one fluid lumen and at least one gas lumen oriented to mix the gas and fluid to generate an aerosol mist inside the peritoneum. Any of a number of nebulizing catheters may be utilized, such as those described in U.S. Pat. No. 5,964,223, issued Oct. 12, 1999 and entitled "Nebulizing Catheter and Methods of Use and Manufacture", the entirety of which is incorporated by reference herein. Some examples of nebulizing catheters are shown in FIGS. 2-4.

Figure 2:
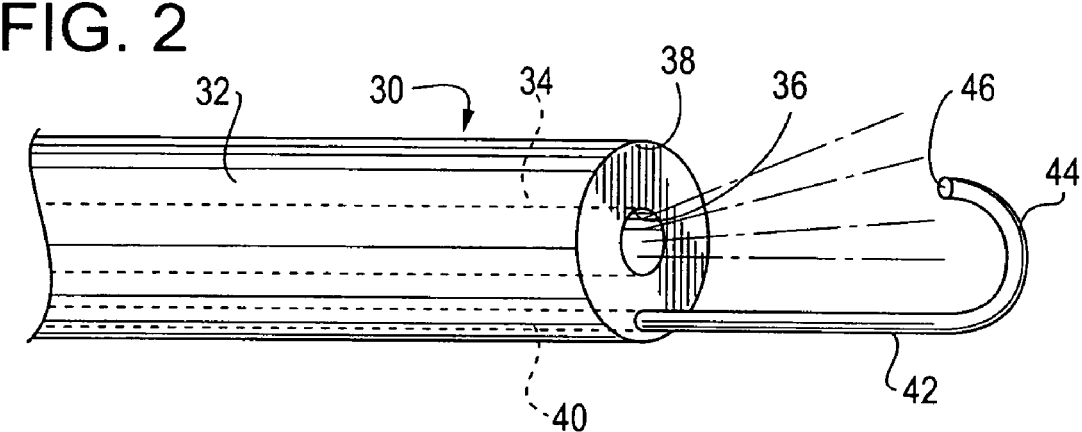
FIG. 2 is a perspective view of a nebulizing catheter suitable for use in the system of FIG. 1.

FIG. 2 shows a nebulization catheter 30 with a distal end that can be located inside of a peritoneum via a trocar. The nebulization catheter 30 has a coaxial tubular arrangement with an outer tube 32 surrounding an inner tube 34 so that a fluid delivered from a distal liquid orifice 36 of the inner tube 34 is nebulized by the flow of a pressurized gas delivered in a distal direction from the annular region between the inner and outer tubes at the distal orifice 38 of the outer tube 32. In addition, another lumen 40 extends through the shaft of the nebulization catheter 30. This additional lumen 40 connects to a distal tubular extension 42. The tubular extension 42 extends distally of the distal end of the nebulization catheter 30. A distal end 44 of the distal tubular extension 42 curves back on itself so that a distal orifice 46 of the tubular extension 42 is oriented in a proximal direction back at the orifices 36 and 38 of the inner and outer tubes.

The additional lumen 40 also carries a pressurized gas which is directed in a proximal direction by the orifice 46 against the direction of the aerosol plume generated by the gas and liquid exiting the orifices 36 and 38. The gas from the additional lumen 40 presents a counterflow to the gas from these orifices thereby slowing down the velocity of the particles generated from these orifices. In a preferred embodiment, the distal tubular extension 42 may be formed of a suitable material such as stainless steel needle stock.

Figure 3:
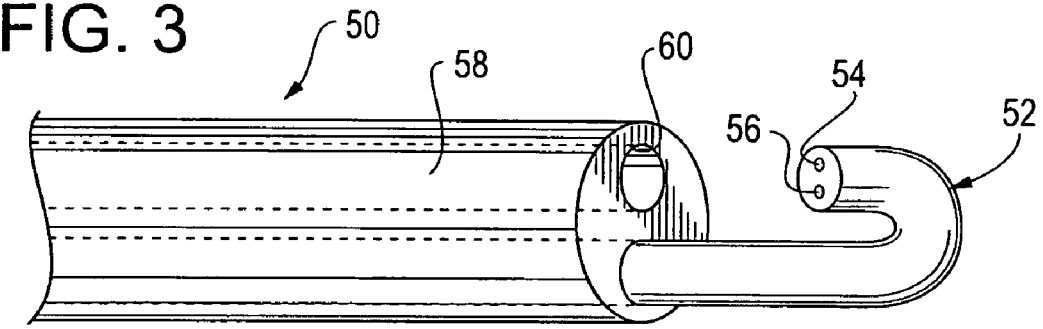
FIG. 3 is an alternative embodiment of the nebulizing catheter of FIG. 2.
Figure 4:
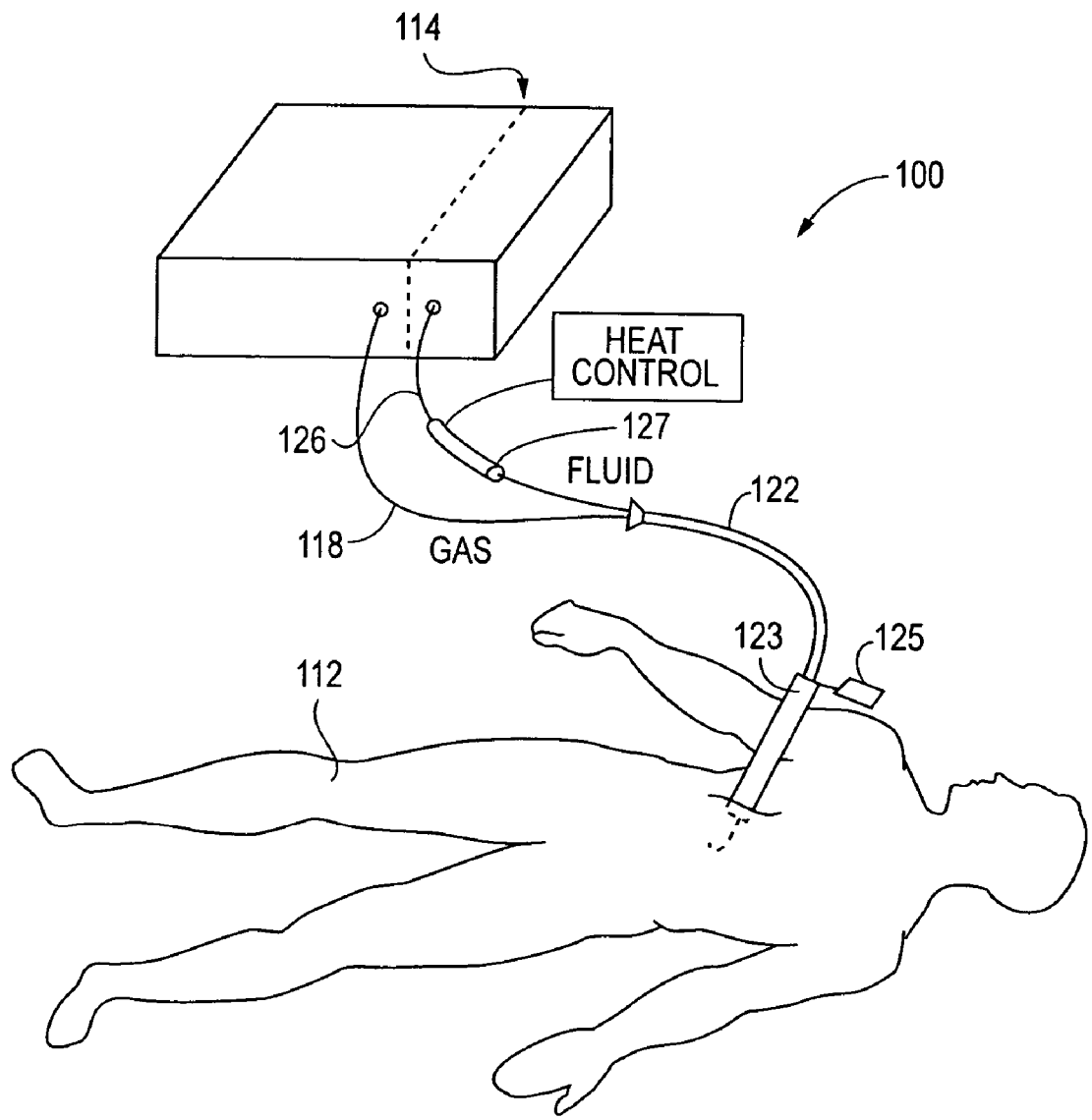
FIG. 4 is an alternative embodiment of the system of FIG. 1.

FIG. 3 shows another embodiment of a nebulizing catheter 50 that incorporates a counterflow arrangement. Like the embodiment described above, in this embodiment the nebulizing catheter 50 may be positioned in a trocar. The nebulization catheter 50 has a distal section 52 that curves back on itself. The nebulization catheter 50 has distal orifices 54 and 56 that generate a plume of nebulized particles in a reverse, i.e. proximal, direction. Also located in the nebulization catheter 50 is another lumen 58 for carrying a pressurized gas. The additional lumen 58 has a distal orifice 60 oriented in a distal direction. The distal orifice 60 of the additional lumen 58 is aligned with respect to the distal orifices 52 and 54 of the nebulization catheter 50 so that the flow of gas from the additional lumen 58 down the velocity of the nebulization plume generated from the nebulization catheter 50. The aerosol plume generated by the nebulization catheter reverses direction and is delivered to the peritoneum carried by the flow of gas from the additional lumen 58.

In another embodiment of a nebulization catheter arrangement, the catheter may include three lumens, two gas and one liquid, where the second of the two liquid lumens is utilized to sense pressure and/or provide pressure relief to the body cavity.

Referring to FIG. 4, an alternative embodiment of the system 100 is shown. In this embodiment, the system 100 provides both the insufflation gas and the aerosolization gas through a single gas line 118 that is routed through the nebulization catheter 122 via the trocar 123 or other needle inserted into the patient 112. A combined insufflator/pump 114 provides both the insufflation gas and the fluid through the nebulizing catheter 122. The fluid is provided along a fluid line 126 that may pass through an optional heating sleeve 127 controlled by a heater controller 128 to warm the fluid to a desired temperature. In an alternative embodiment, the fluid heating mechanism may be integral with the pump or provided by an in-line heater. In another embodiment, where the pump is a syringe pump for controlling fluid discharge from a removable syringe, heat may be supplied to the fluid using syringe heater tape available from Watlow Electric Manufacturing Co. of St. Louis, Mo. The heater may be controlled through a central controller at the combination insufflator/pump 114. The temperature of the fluid is preferably adjusted such that heat loss in the remaining path to the body cavity is accounted for so the fluid is within the desired temperature range as it enters the body cavity. A relief valve mechanism 125 is provided to control the gas pressure so that the gas pressure in the peritoneum or other body cavity is maintained at a desired level. The pressure relief valve 125 may be integrated with the trocar or may be a separate relief valve mechanism positioned along the gas line 118 or in the insufflator. As illustrated in FIG. 4, the system 100 may include combined or separate gas and fluid sources. Additionally, the system may work through a single trocar 123 or through separate trocars as is illustrated in the embodiment of FIG. 1.

Figure 5:
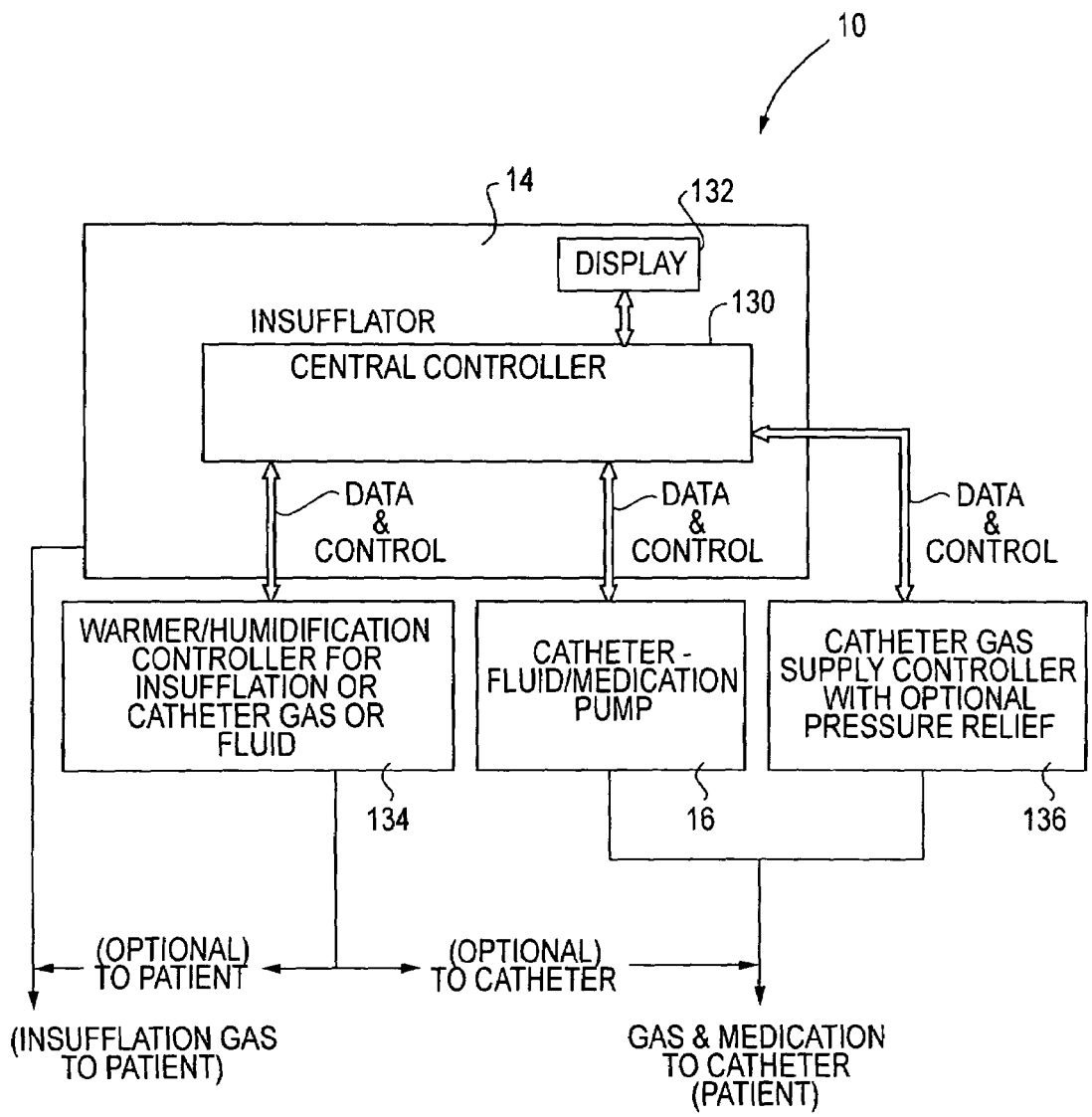
FIG. 5 is a schematic view of an embodiment of control connections of the system of FIG. 1.

As shown in FIG. 5, the system 10 of FIG. 1, is preferably controlled by a central controller 130 which may be integral with, or separate from, the insufflator 14. The insufflator may also include a display 132 for simultaneously or selectively displaying one or more of the parameters managed by the central controller 130. Preferably, the central controller 130 is in communication with each of the components of the system, whether integrated with the insufflator 14 or discrete. Thus, the central controller 130 may monitor and adjust the temperature and humidification control of the insufflation and catheter gas via the gas controller 134, the operation of the pump 16 providing medication to the catheter and the controller 136 connected with the pressure relief valve or valves on the insufflation gas supply and/or the catheter gas supply. One or more of the controllers 130, 134, 136 and the display 132 may be integrally formed with, or independent of, the insufflator 14. The display may be provided with one or more standard interface buttons, or a touch screen capability. Any of a number of communication protocols and formats may be used between the central controller 130 and any of the integrated or discrete controllers.

Figure 6:
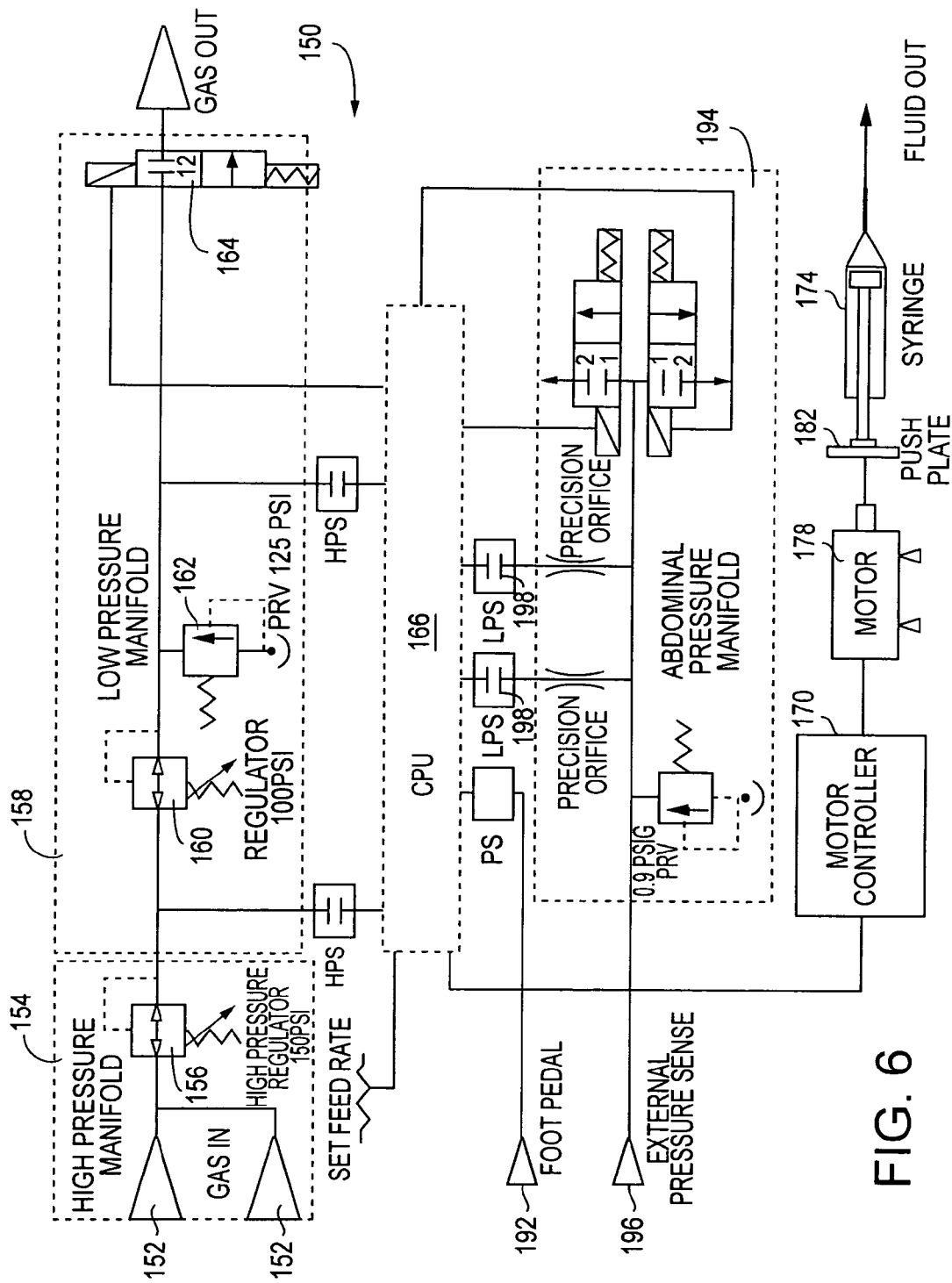
FIG. 6 is a block diagram of a regulated liquid and gas dispensing controller suitable for use in the system of FIG. 1.

A more detailed diagram of an embodiment of a regulated liquid and gas dispensing controller 150 incorporating a syringe pump, independent CPU and optional active pressure relief mechanism as shown in FIG. 6. The controller 150 combines insufflator and pump controller tasks. In one embodiment, the controller is preferably configured in a high pressure, low flow arrangement that differs from the typical low pressure, high flow arrangement of insufflators generally. Insufflation gas from a high pressure gas source, such as pressurized bottled gas, is connected at the gas inputs 152. A high pressure manifold 154 regulates the pressure from the initial high pressure source, in which gas can be at a pressure in the range of 2000 p.s.i., and reduces the supply pressure through a high pressure regulator 156. In one embodiment, the high pressure regulator 156 reduces the received gas pressure to approximately 150 p.s.i. Any of a number of types of high pressure regulators may be used.

The pressure of insufflation gas supplied to a patient generally needs to be at a lower pressure and so the gas from high pressure manifold at, for example, 150 p.s.i. is then processed through a low pressure manifold 158. The low pressure manifold includes a low pressure regulator 160 configured to further reduce the gas pressures. In this example, the gas pressure is reduced from 150 p.s.i. to 100 p.s.i. This pressure translates to a flow rate of 2-3 liters per minute actually introduced to the body cavity due. The pressures discussed above are merely presented as examples and the various pressure settings in the high and low pressure manifolds may be user adjustable, or may be preset at the manufacturer with no manual settings necessary, at any of a number of pressures. The low pressure manifold also includes a passive pressure relief valve (PRV) 162 set to mechanically release pressure above a predetermined threshold which, in this example, is 0.9 pounds per square inch gauge (p.s.i.g.). An electrically controllable output valve 164 meters the gas output sent on to a catheter. Pressure monitor lines connect a central processor (CPU) 166 to the low pressure manifold via high pressure sensors 168. When used in an insufflator arrangement, at least one of a passive pressure relief valve 24 (See FIG. 1) at the patient may be used to control the pressure introduced to the patient, or the optional active pressure controller 194, described in more detail below, may be utilized. The syringe pump motor controller 170 is also controlled by the CPU to meter the amount of fluid provided to a patient.

An actuator 192 may be connected with the controller 150 to initiate one or more actions by the controller 150. For example, the actuator 192 may send a signal to the CPU 166 that will start or stop the production of insufflation gas, the dispensing of fluids or other activities. In one embodiment, the actuator 192 may be a foot pedal or some other form of actuator that allows a medical practitioner to keep both hands free. Push buttons, levers, touch-screens or any of a number of actuation input means are also contemplated.

An optional portion of the regulated liquid and gas dispensing controller is an active pressure controller 194 that, in addition to the mechanical, passive pressure relief valve 162, can provide a mechanism for limiting pressure supplied to the patient. Although optional, the active pressure controller 194 can provide more precise pressure control by taking a pressure measurement supplied from a sensor via an external pressure sense line 196 at the patient's body and allowing the CPU 166 to actively regulate the pressure. Pressure data may be provided to the CPU 166 by way of low pressure sensors 198. The active pressure controller can reduce the pressure supplied to the patient through one or more active pressure relief valves electrically controllable by the CPU.

Figure 7:
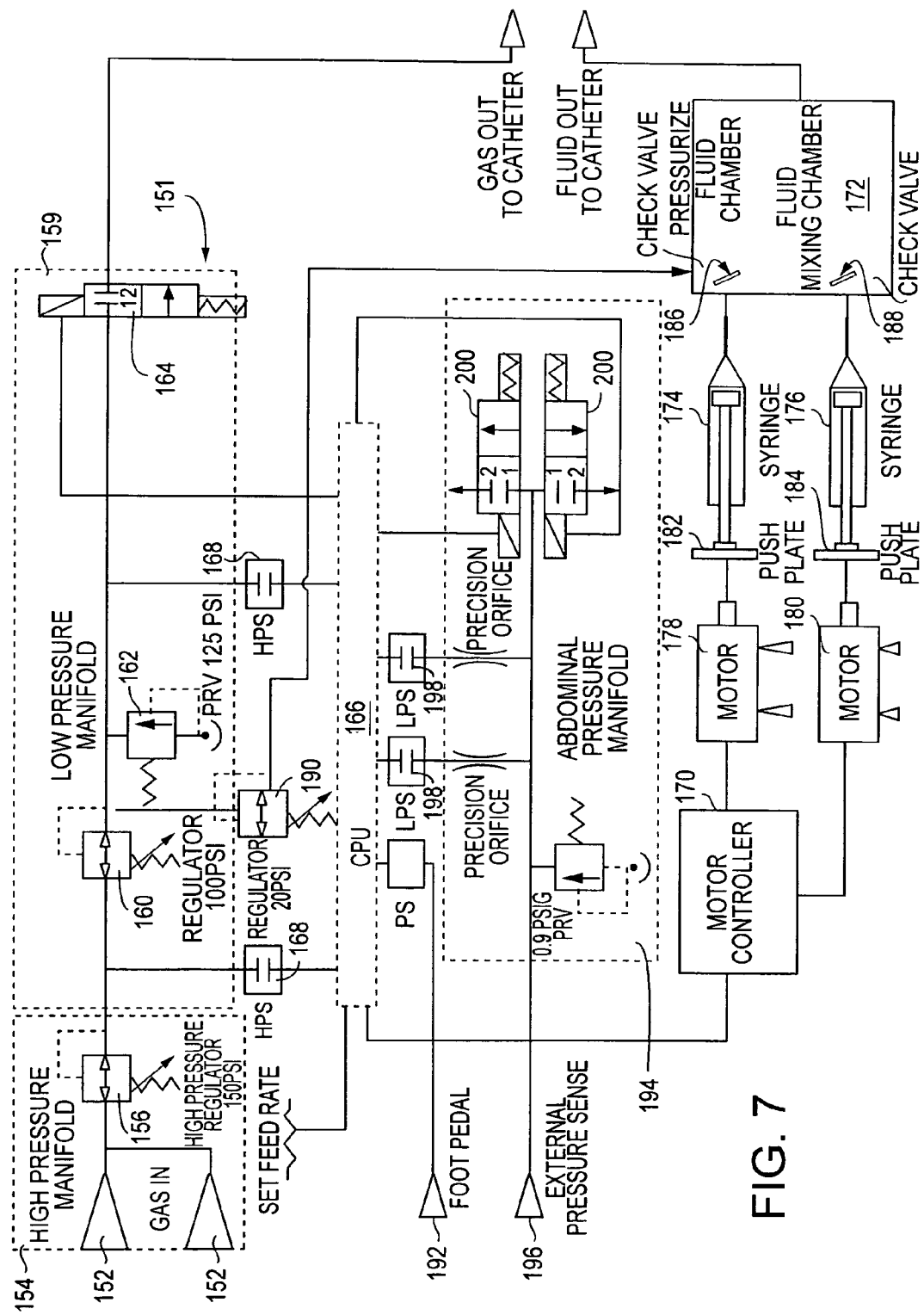
FIG. 7 is a block diagram of an alternative embodiment of the regulated liquid and gas dispensing controller of FIG. 6 having a fluid mixing chamber for dispensing and mixing multiple fluids.

Some operative and post-operative therapies may require a mixture of more than one fluid. The fluid mixture can be achieved through a number of minor modifications. One embodiment of a regulated liquid and gas dispensing controller 150 with multiple fluid sources is illustrated in FIG. 7. In the embodiment of FIG. 7, a mixture of fluids is provided by a configuration of the regulated liquid and gas dispensing controller 151 that utilizes a fluid mixing chamber 172 to mix different fluids provided by separate syringes 174, 176. The motor controller 170 interprets instructions from the CPU 166 to activate the separate motors 178, 180 linked to push plates 182, 184 to engage the respective syringes 174, 176.

Upon a signal from the CPU 166 and motor controller 170, each motor 178, 180 will move its push plate a certain metered distance and cause the syringe to eject a measured amount of fluid into the fluid mixing chamber 172. Each motor 178, 180 may be instructed to move the same or different amount depending on the desired mixture of fluids. Check valves 186, 188 may be included on the input ports of the fluid mixing chamber as added protection against back flow into the same or different syringe. In order to provide sufficient pressure to eject the mixture of fluid from the fluid mixing chamber, such as a 20 p.s.i. or other low pressure regulator, supply of gas from the low pressure manifold 159 is taken after the low pressure regulator 160 and further processed through a mixing chamber pressure regulator 190 down to, in this example, 20 p.s.i. The gas is then transmitted to the fluid mixing chamber to propel the mixed fluid to the catheter for nebulization in a body cavity, for topical application or other application. Using this embodiment, the different fluids can be administered in combination or consecutively, where a single fluid is sent through, and evacuated from, the mixing chamber before the next fluid is dispensed.

Figure 8:
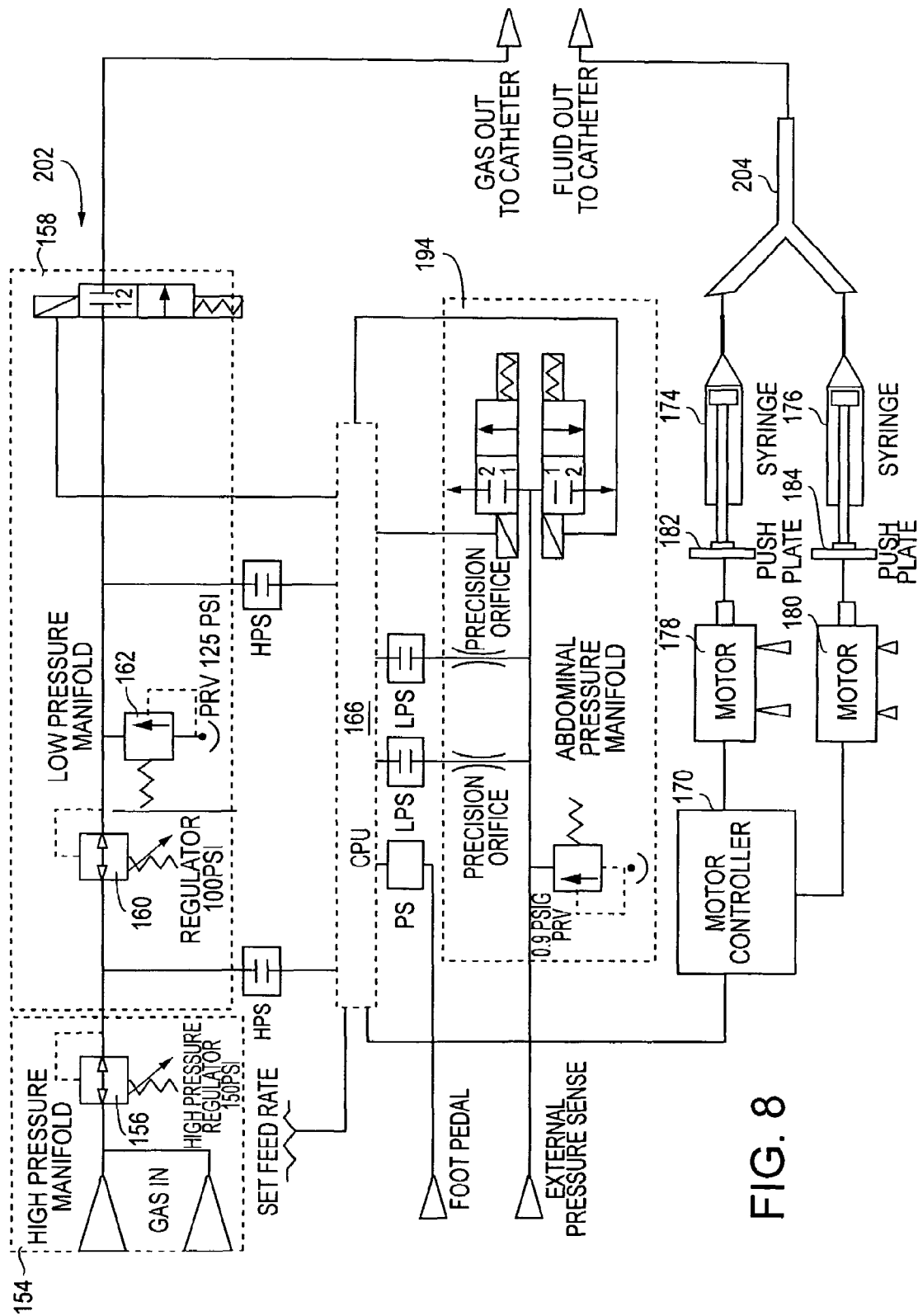
FIG. 8 is a block diagram of a second alternative embodiment of the regulated liquid and gas dispensing controller of FIG. 6 having a y-tube for dispensing and mixing multiple fluids.

Another embodiment of a controller 202 configured for fluid mixture is shown in FIG. 8. In this embodiment, all the same components as in FIG. 7 are identified with the same reference numbers. The embodiment of FIG. 8 differs from that of FIG. 7 in that a passive y-tube 204 replaces the fluid mixing chamber 172 and fluid mixing chamber regulator 190 of FIG. 7. Thus, the mixing of fluids and delivery of the fluid from the syringes 174, 176 to the catheter takes place using the force of the push plates 178, 180 on the syringes. The different fluids may be combined in the y-tube by simultaneously dispensing the fluids from the syringes. Alternatively, the fluids may be dispensed consecutively or at widely spaced time intervals depending on the application.

Figure 9:
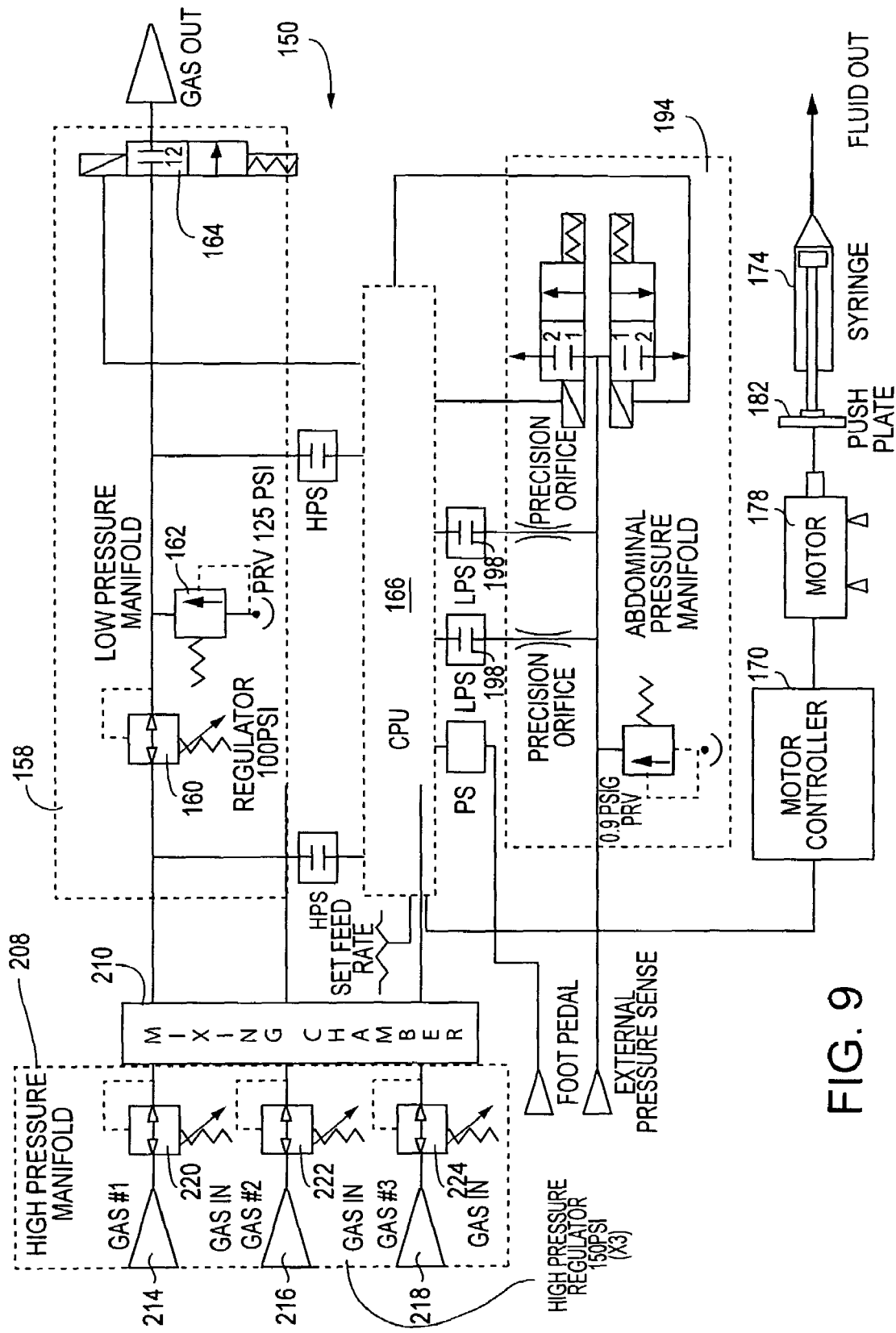
FIG. 9 is a block diagram of a third alternative embodiment of the regulated liquid and gas dispensing controller of FIG. 6 having a gas mixing chamber for providing a mixed insufflation gas.

In addition to providing configurations of a controller for providing a single type of fluid, or multiple types of fluids, embodiments of the present invention include configurations and methods for accommodating multiple different gases. In one embodiment, shown in FIG. 9, a modified high pressure manifold 208 and mixing chamber 210 in a controller 212 may be used to replace the high pressure manifold 154 of FIGS. 6 and 7. The remaining components of the controller 212 in FIG. 8 identical to those in FIGS. 6 and 7 retain the same reference numerals for clarity. Using the controller 212 of FIG. 8, a mixture of different insufflation gases 214, 216, 218 are processed in respective high pressure regulators 220, 222, 224 to bring their pressures down to a lower pressure, 100 p.s.i. in this example, more easily managed by the mixing chamber 210. The mixing chamber, an example of which is disclosed in U.S. application Ser. No. 10/829,485 incorporated above, combines substantially even amounts of the gases into a mixture that is then processed through the low pressure manifold 158 as previously described. Examples of applications for mixed gas insufflation include the prevention of acidosis through the addition of oxygen to the insufflation gas, the reduction of post-operative pain through the addition of helium or oxygen, and other such applications.

Figure 10:
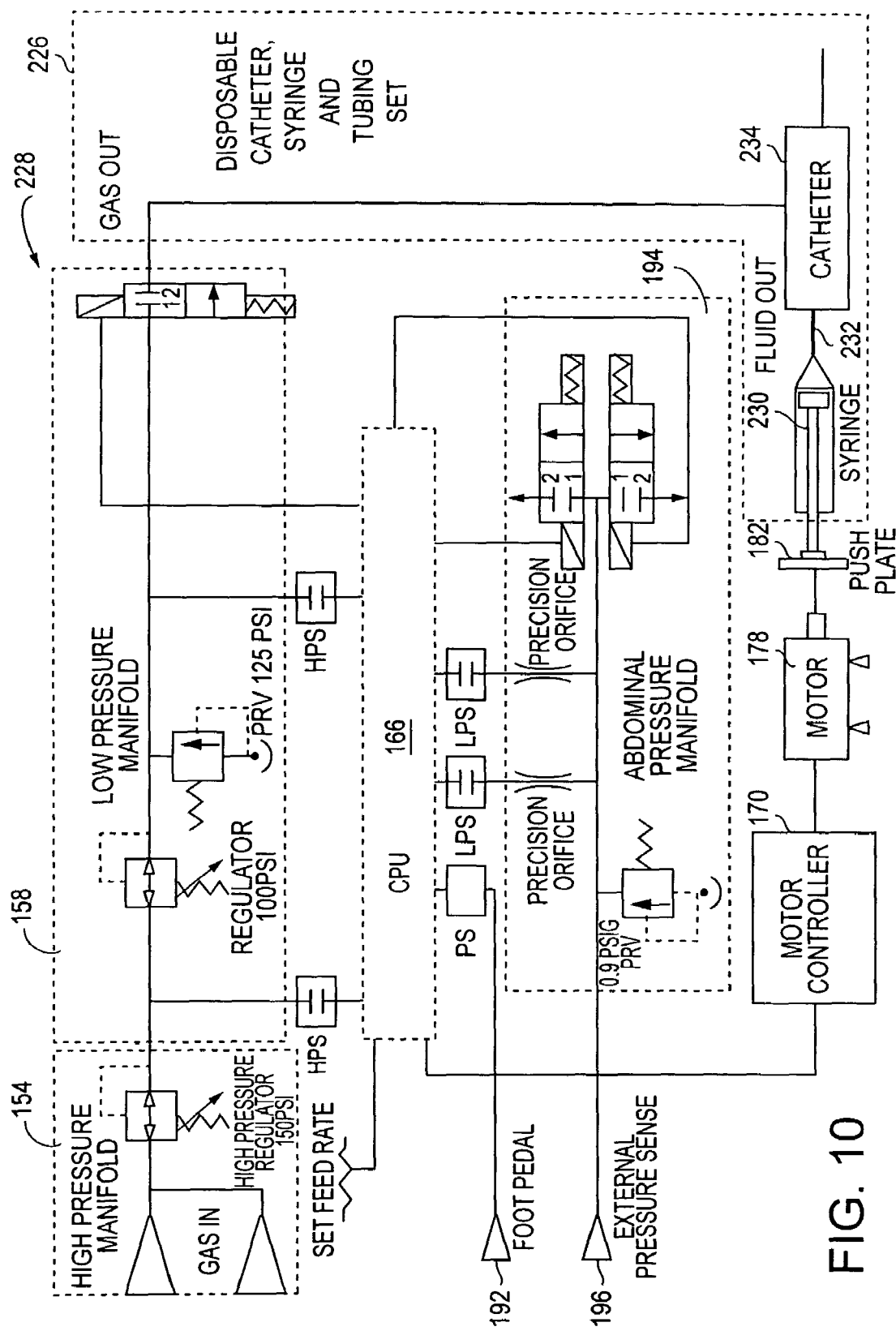
FIG. 10 is a block diagram of a disposable catheter, syringe and tubing set attached to the regulated liquid and gas dispensing controller of FIG. 6.

In another embodiment, the fluid pump assembly of the regulated liquid and gas dispensing controller, which includes the motor controller 170, motor 178, and push plate 182, may be adapted to work with a disposable catheter, syringe and tubing set 226. As shown in FIG. 10, the set allows for increased isolation of any fluid from contact with the rest of the controller 228. This is achieved by including a direct syringe 230 to tube 232 to catheter 234 connection rather than a separate, fixed syringe holder that encloses a syringe on the interior of the holder and attaches a tube to the outside of the syringe holder where fluid contacts a conduit built into the holder between the syringe and catheter or tube. To provide further isolation from contamination, the tube 236 or other conduit from the gas outlet of the low pressure manifold to the catheter is also preferably part of the set 226.

Figure 11:
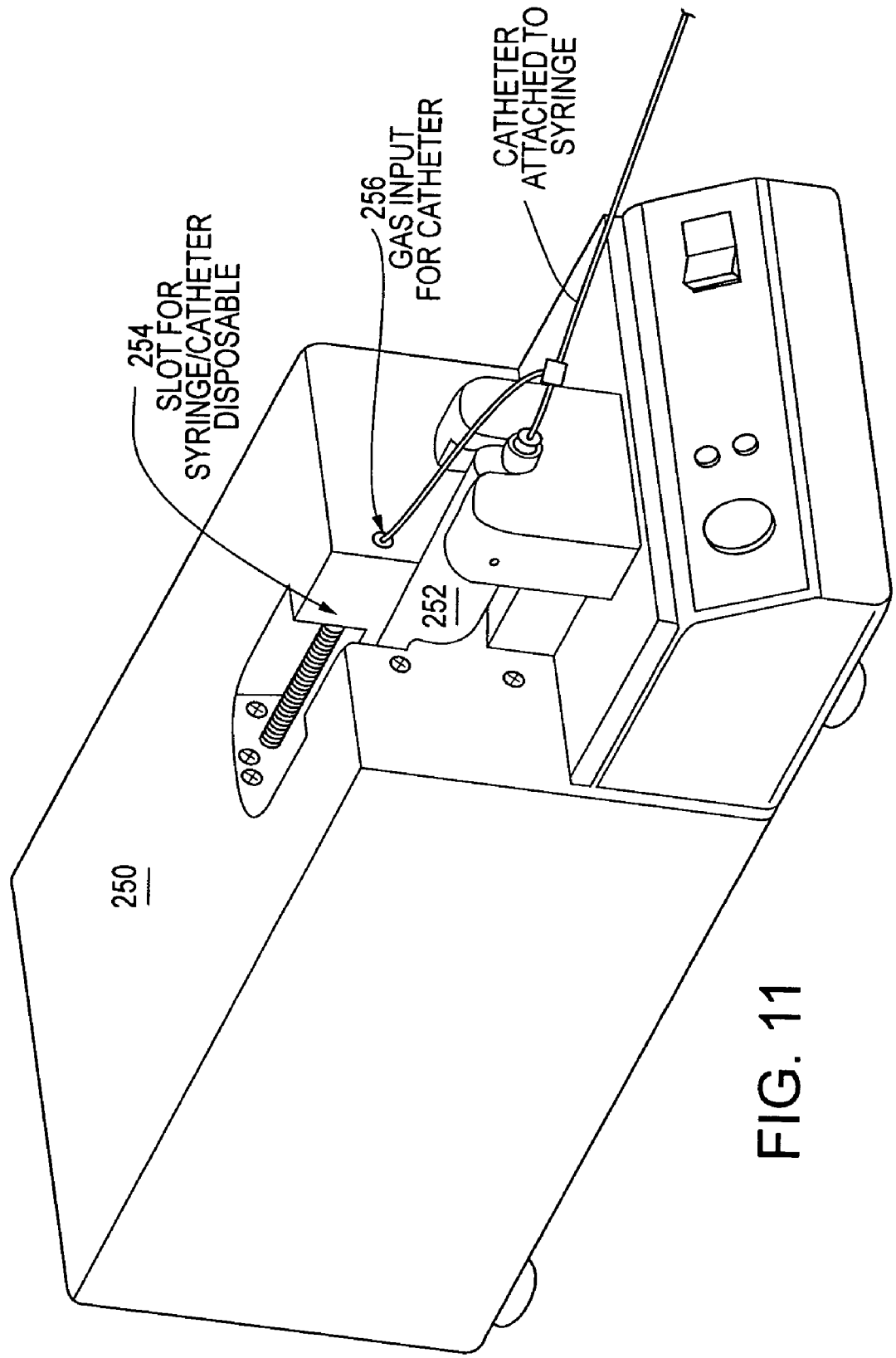
FIG. 11 is a perspective view of a syringe pump having a receiving slot for a disposable syringe/catheter/tubeset.

FIG. 11 discloses a perspective view of a syringe pump assembly 250 having a receiving slot 254 for a disposable syringe/catheter/tubeset. The catheter (not shown) may be preassembled as attached to the syringe 252 and replaceably insertable with the syringe as the syringe is place into the receiving slot 254 the syringe pump assembly, or the catheter may be separated from the syringe and still directly attached to the syringe without any intervening, non-disposable lumen. The syringe pump assembly 250 may be in communication with a remote processor or contain its own processor for managing operation of the syringe pump and any gas supply that may also be incorporated. In one embodiment, the housing of the syringe pump assembly may also contain pneumatics for supplying insufflation/catheter gas so that all the elements of the regulated liquid and gas dispensing controller discussed previously are maintained in a single housing. In this embodiment, a catheter gas input port 256 may be integrally formed in the assembly so that a gas may be provided to the catheter attached to a syringe mounted in the assembly. A passive pressure relief valve located at the patient may be used to control insufflation pressure or the assembly 250 may contain an active pressure relief valve. In the embodiment where an active pressure relief valve is incorporated, a pressure sense port for communicating with a pressure sense line from a patient would also be integrated into the housing of the assembly.

Utilizing the integrated system or separate system components described above, a method of providing a substance, such as a nebulized medication, to a body cavity during a minimally invasive procedure is now described. Although a laparoscopic procedure is specifically identified below, the applications of medication using this system can include administration of nebulized substances onto or into specific organs and lumens in the body, as well as topical applications. Additionally, the systems and methods described herein are applicable to minimally invasive procedures generally. In many normal laparoscopic procedures, such as for gall bladders, hernias, bowl resections and etc., a patient is placed in the prone position and sedated. A verres-type needle is placed in the patient to transport gas to the patient and this verres needle is connected to the insufflator to pump up the peritoneum. One suitable verres needle or, more generally, insertion device is disclosed in U.S. application Ser. No. 09/841,125, filed Apr. 24, 2001 and published on Dec. 5, 2002 as Pub. No. US 2002/0183715, the entirety of which is incorporated herein by reference. The verres needle may then be removed and a trocar inserted through the needle hole already made, while maintaining a supply gas in the cavity. Using the opening provided by the trocar, an endoscope is inserted so that a physician may see inside the body. At this point, several other smaller trocars may be inserted into the body for instruments to be used as needed for the particular procedure.

Utilizing the system described above, the insufflation gas is preferably heated and humidified, and an appropriate medicament treatment is applied. For example, to avoid adhesion problems which may often occur in laparoscopic procedures, an aerosol can be provided via the aerosolization catheter to cover the exposed organs and wall of the abdomen. This anti-adhesion treatment may be repeated multiple times during a surgical procedure and be preprogrammed into the central controller 130 of the system. During the procedure, the parameters relating to the delivery of gas and fluid may be displayed and individually controlled. The parameters may include humidity, temperature, pH, volume, rate, pressure, and duration of any of the fluid or gas being injected into the patient. The pH may be adjusted by, for example, the introduction of acid or buffer solutions to the fluid. While any of a number of catheters may be used with the various embodiments of the regulated liquid and gas dispensing controller to apply a medication, or supply both the insufflation gas and a medication, two suitable catheters are disclosed in U.S. Pat. Nos. 6,379,373, issued Apr. 30, 2002, and 6,165,201, issued Dec. 26, 2000. The disclosure of both of these U.S. patents is incorporated herein by reference.

With the system and method described above, a physician may apply an aerosolized medicament to a distended body cavity that will allow for efficient, safe and effective application of any number of potentially aerosolized liquids which can be used for pain and management (analgesics), infection prevention (prophylactic antibiotics), tissue adhesion (any number of formulations can be used including naturally occurring lubricious medications such as hyaluronic acid, or any number of other medicaments such as heparin, glycerin or glycol medications, or even humidity), and tumor prevention (using targeted or prophylactic chemotherapy drugs or methods) or to control bleeding or blood clotting. Although laparoscopic procedures are specifically discussed above, the systems and methods disclosed herein are contemplated for use in any endoscopic or other minimally invasive procedure.

With reference to targeted or prophylactic chemotherapy, according to another aspect of this invention, the system may be used for general continued, and post-operative applications of a substance by re-instituting an environment in the patient in which subsequent applications of the substance, such as an aerosolized medication, may be administered. This may be accomplished by leaving a port device in the patient after a surgical procedure, or by surgically placing a port in the patient in preparation of a non-surgical treatment regimen. The port may be any device capable of providing a sanitary access point to a body cavity, where the device is a resealable mechanism that attaches to the exterior of the abdomen and the interior wall of the abdomen. One example of a suitable port is an enteral feeding tube port. The port permits the device for applying a substance to the body cavity, in this instance a nebulizing catheter, and the remainder of the system 10 of FIG. 1 to be reconnected to the patient at a later time to apply the substance or other treatment. In one embodiment, the substance may be an analgesic to assist with post-operative pain. In another embodiment, the substance may be an antibiotic for application sometime after surgery to combat infection that may arise.

Alternatively, independently of any post-operative pain or infection, a patient may be provided with such a port for the purpose of allowing an effective chemotherapy treatment. In this situation, a patient would be provided with the port so that the organ or organs affected by a cancer may be directly treated with aerosol treatment customized for that particular patient or tumor. In either situation, post-operative reentry or chemotherapy application, treatment may be accomplished without an endoscope. In some embodiments, an endoscope may be used to allow a medical professional to properly apply the aerosol to the desired region and so that a distal end of a nebulizing catheter may be oriented to provide optimal aerosol placement. During the re-entry into the peritoneum, the pressure relief valve or valves (active or passive) are used to maintain a safe cavity pressure. By maintaining proper pressure within the peritoneum, any additional pressure introduced by the gas used in the aerosolization of the medicine, or pressure from the introduction of fluids or other substances from outside the body cavity may be accounted for.

As discussed above, a method and apparatus for creating a medicated atmosphere in an organ or body cavity has been disclosed. The method permits a creation of an aerosol cloud allowing for the deposition of a substance comprising a medicament on all or a selected number of interior surfaces. The apparatus comprises an aerosolization catheter that can be manipulated during use, a device for the introduction of the aerosolization catheter, a medication delivery system linked to a control means for the control of rate, amount, and time of delivery of the medication, a system for providing pressure control of a gas to the catheter which is also controlled as to pressure, timing and rate of gas flow, a means for monitoring and relieving the pressure of the gas, alone or in conjunction with an insufflator, and a means of integrating the control of the various gas and fluid supplies for complete system control. Additionally, means for reentering the peritoneum or organ post-operatively to recreate a medicated environment for a post-operative treatment is disclosed. The insufflation and nebulization may both be performed through a single gas lumen in a catheter, or multiple gas lumens, using the same regulated liquid and gas dispensing controller.

It is intended that the foregoing detailed description be regarded as illustrative rather than limiting, and that it be understood that the following claims, including all equivalents, are intended to define the scope of this invention.

I claim:

1. A system for providing a controlled environment in a body cavity of a patient, the system comprising:

- an insufflator adapted to provide a supply of gas to the body cavity via a gas line;
- a nebulizing catheter in communication with a source of nebulizing gas and a source of fluid for nebulizing, the nebulizing catheter having a distal end positionable in the body cavity and configured to generate an aerosol at the distal end within the body cavity;
- at least one pressure relief valve in communication with one of the gas line or the source of nebulizing gas, the at least one pressure relief valve for maintaining a pressure in the body cavity; and
- a central controller in communication with the insufflator, the source of nebulizing gas, the source of fluid and the pressure relief valve to coordinate delivery of fluid and gas, while maintaining a desired pressure in the body cavity, wherein the central controller is configured to monitor and adjust delivery of fluid by the source of fluid to the nebulizing catheter.

2. The system of claim 1, wherein the at least one pressure relief valve comprises one of an electrically or pneumatically controllable valve.

3. The system of claim 1, wherein the at least one pressure relief valve comprises a passive mechanical valve.

4. The system of claim 1, wherein the system comprises a system for performing a laparoscopic procedure for providing the controlled environment in the body cavity of the patient.

5. A system for use in a minimally invasive procedure to deliver a substance to a body cavity of a patient, the system comprising:

- a fluid dispensing controller in communication with a gas supply and the substance;
- a catheter configured for insertion into the body cavity, the catheter comprising:
  - a gas delivery channel configured for delivery of gas from the gas supply to the body cavity of the patient, wherein the gas delivery channel comprises an only source of gas provided to the body cavity; and
  - a substance delivery channel configured for delivery of the substance to the body cavity of the patient; and
  - the gas delivery channel and the substance delivery channel extending separately into, and terminating within, a distal end positionable in the body cavity, wherein the distal end is configured to cause gas from the gas delivery channel to mix with the substance from the substance delivery channel outside the gas delivery channel and substance delivery channel and within the body cavity to form an aerosol;
- at least one pressure relief valve in communication with one of the gas and substance delivery channels for maintaining a pressure in the body cavity; and
- wherein gas delivered to the body cavity via the gas delivery channel both distends the body cavity and nebulizes the substance.

6. The system of claim 5, wherein the pressure relief valve comprises a passive pressure relief valve configured for positioning adjacent the body cavity.

7. The system of claim 5, wherein the pressure relief valve comprises an active pressure relief valve positioned adjacent the gas supply and in communication with the body cavity via an external pressure sense line.

8. The system of claim 5, wherein the fluid dispensing controller comprises a housing sized to removably receive a disposable syringe.

9. The system of claim 8, further comprising a disposable catheter defining at least a portion of the gas delivery channel, the disposable catheter operatively connected with the disposable syringe via one of a direct connection or a disposable tube.

10. The system of claim 5, further comprising a plurality of syringes in communication with the substance delivery channel and independently controllable by the fluid dispensing controller to provide a plurality of fluids to the substance delivery channel.

11. The system of claim 10, wherein the plurality of syringes are in communication with the substance delivery channel via a mixing chamber.

12. The system of claim 11, wherein the mixing chamber is connected to a pressurized gas supply.

13. The system of claim 5, wherein the minimally invasive procedure comprises and endoscopic procedure.

14. The system of claim 13, wherein the endoscopic procedure comprises a laparoscopic procedure.

* * * * *